US010307436B2

(12) United States Patent
Kim et al.

(10) Patent No.: US 10,307,436 B2
(45) Date of Patent: Jun. 4, 2019

(54) COMPOSITION CONTAINING GINSENOSIDE F1 FOR REMOVING AMYLOID PLAQUES

(71) Applicant: INTELLIGENT SYNTHETIC BIOLOGY CENTER, Daejeon (KR)

(72) Inventors: Sun Chang Kim, Daejeon (KR); Jin Hee Han, Daejeon (KR); Bong Hwan Park, Yongin-si (KR)

(73) Assignee: INTELLIGENT SYNTHETIC BIOLOGY CENTER, Daejeon (KR)

( * ) Notice: Subject to any disclaimer, the term of this patent is extended or adjusted under 35 U.S.C. 154(b) by 123 days.

(21) Appl. No.: 15/193,444

(22) Filed: Jun. 27, 2016

(65) Prior Publication Data
US 2017/0027969 A1 Feb. 2, 2017

(30) Foreign Application Priority Data

Jul. 27, 2015 (KR) .................. 10-2015-0106011

(51) Int. Cl.
*A61K 31/704* (2006.01)
(52) U.S. Cl.
CPC .................. *A61K 31/704* (2013.01)
(58) Field of Classification Search
None
See application file for complete search history.

(56) References Cited

U.S. PATENT DOCUMENTS

2005/0245465 A1* 11/2005 Kim .............. C07H 15/24
15/24

FOREIGN PATENT DOCUMENTS

| CN | 1839855 A * | 10/2006 | ........... A61K 31/704 |
|---|---|---|---|
| EP | 1 024 146 A1 | 8/2000 | |
| JP | 2003212776 A | 7/2003 | |
| JP | 2006512384 A | 4/2006 | |
| JP | 2007518795 A | 7/2007 | |
| JP | 2011502117 A | 1/2011 | |
| WO | 2006/019685 A2 | 2/2006 | |

OTHER PUBLICATIONS

Qiu, J., Li, W., Feng, S. H., Wang, M., & He, Z. Y. (2014). Ginsenoside Rh2 promotes nonamyloidgenic cleavage of amyloid precursor protein via a cholesterol-dependent pathway. Genet Mol Res, 13(2), 3586-98. (Year: 2014).*
Callahan, M. J., Lipinski, W. J., Bian, F., Durham, R. A., Pack, A., & Walker, L. C. (2001). Augmented senile plaque load in aged female β-amyloid precursor protein-transgenic mice. The American journal of pathology, 158(3), 1173-1177. (Year: 2001).*
Lee, J. W., Choi, B. R., Kim, Y. C., Choi, D. J., Lee, Y. S., Kim, G. S., . . . & Lee, D. Y. (2017). Comprehensive profiling and quantification of ginsenosides in the root, stem, leaf, and berry of Panax ginseng by UPLC-QTOF/MS. Molecules, 22(12), 2147. (Year: 2017).*
Chen F et al., "Reductions in levels of the Alzheimer's amyloid [beta] peptide after oral administration of ginsenosides", FASEB Journal, vol. 20, No. 8, Jun. 2006, pp. E599-E604.
Gyu Y S et al., "Composition Health Food Prevent Treat Hypertensive Angina Comprise Ginsenoside Separate Leaf Stem Bud Ginseng", Database WPI Week 201219 Thomson Scientific , London, GB; AN 2011-C55486, KR101016996B1(Univ Ind &Academic Coop in Chungnam Nat) Feb. 28, 2011.
Korean Office Action, Korean Patent Application No. 10-2015-0148337, dated Jan. 6, 2017.
Lu Jian-Ming et al., "Ginseng compounds: an update on their molecular mechanisms and medical applications", NIH Public Access Author Manuscript, Aug. 2010, pp. 1-18, Retrieved from the Internet: URL:https://www.ncbi.nlm.nih.gov/omc/articles/PMC2928028/pdf/nihms227605.pdf, 293-302.
Quan, Qiankun et al., Ginsenoside Rg1 Decreases Aβ 1-42 Level by Upregulating PPARγ and IDE Expression in the Hippocampus of a Rat Model of Alzheimer's Disease, PLOS ONE, Mar. 2013, vol. 8, Issue 3 e59155, pp. 1-8.
Qiu J et al., "Ginsenoside Rg1 Decreases Ab1-42 Level by Upregulating PPARc and IDE Expression in the Hippocampus of a Rat Model of Alzheimer's Disease," Genetics and Molecular Research, vol. 13, No. 2, 2014, pp. 3586-3598.
Veerappan, Karpagam et al., "Identification of BACE1 inhibitors from Panax ginseng saponins-An Insilco approach," Computers in Biology and Medicine, 43, 2013, 1037-1044.
Veronese, Andrea, Extended European Search Report, European Patent Application No. 16176398.2, dated Jan. 17, 2017.
Yang, Lingling et al., "Ginsenoside Rg3 promotes beta-amyloid peptide degradation by enhancing gene expression of neprilysin", Journal of Pharmacy and Pharmacology, vol. 61, Issue 3, Mar. 2009, pp. 375-380.
Selkoe, Dennis J., "Translating cell biology into therapeutic advances in Alzheimer's disease," Nature. 399(6738 Suppl):A23-31, Jun. 24, 1999.
Chen et al., "Reductions in levels of the Alzheimer's amyloid [beta] peptide after oral administration of ginsenosides", FASEB Journal, vol. 20, No. 8, Jun. 2006, pp. 1269-1271.
DeMattos et al., "A plaque-Specific Antibody Clears Existing B-amyloid Plaques in Alzheimer's Disease Mice," Neuron, vol. 76, pp. 90-920, Dec. 8, 2012.

* cited by examiner

*Primary Examiner* — Eric Olson
*Assistant Examiner* — Dale R Miller
(74) *Attorney, Agent, or Firm* — Gavrilovich, Dodd & Lindsey LLP

(57) ABSTRACT

Provided are a food composition and a feed composition for removing amyloid plaques, each composition including ginsenoside F1, in which ginsenoside F1 is effective for removing amyloid plaques in the hippocampal area of the brain.

6 Claims, 6 Drawing Sheets

COMPOSITION CONTAINING GINSENOSIDE F1 FOR REMOVING AMYLOID PLAQUES

CROSS REFERENCE TO RELATED APPLICATIONS

The application claims priority under 35 U.S.C. § 119 to Korean Patent Application No. 10-2015-0106011, filed Jul. 27, 2015, the disclosure of which is incorporated herein by reference.

BACKGROUND OF THE INVENTION

1. Field of the Invention

The present invention relates to a food composition for removing amyloid plaques, the food composition including ginsenoside F1 or a sitologically acceptable salt thereof. Further, the present invention relates to a feed composition for removing amyloid plaques, the feed composition including ginsenoside F1 or a sitologically acceptable salt thereof. Furthermore, the present invention relates to a method of removing amyloid plaques, the method including the step of administering ginsenoside F1 to a subject excluding humans.

2. Description of the Related Art

Alzheimer's dementia is a disease that most frequently occurs in the elderly, and about 10% of the population of 65-85 years of age and about 40% of the population over 85 years of age suffer this disease. Alzheimer's dementia was reported at first by the observation of Alois Alzheimer of Germany in 1907, and he observed that nerve cells of hippocampus and neocortex of the brain of Alzheimer's patients were lost and there were abnormal structures such as neurofibrillary tangles (NTFs) which look like tangled bundles of fiber and senile plaques within the cell body of neurons.

Of them, senile plaques, also called amyloid plaques, are extracellular deposits of amyloid peptide surrounded by neuritis, astrocytes, microglial cells or the like, and are found mainly in the limbic structure or association neocortex.

Many studies have been conducted to investigate whether these abnormal tissue properties relate to the pathogenesis of dementia.

Specifically, sporadic Alzheimer's disease (SAD) accounts for most cases of dementia, but there have been no findings supporting that SAD is caused by particular genetic mutations. However, senile plaques and neurofibrillary tangles regarded as the pathological features of dementia are found in patients with sporadic dementia. In particular, excess deposition of beta amyloid protein is commonly found in sporadic dementia and hereditary dementia, suggesting that beta amyloid is presumed to play a major role in the pathogenesis of dementia (Nature, 1999, 399:A23-A31).

Now, on the basis of this, global pharmaceutical companies have been focused on therapeutic agents targeting beta amyloid plaques. However, the therapeutic agents developed until now have weak, temporary efficacy and they also show severe toxicity. There have been few case reports regarding successful clinical trials.

Accordingly, the present inventors have made many efforts to develop a substance capable of removing amyloid plaques which is a cause of Alzheimer's dementia. As a result, they found that a natural substance, ginsenoside F1 has a very excellent effect of removing amyloid plaques, thereby completing the present invention.

SUMMARY OF THE INVENTION

An object of the present invention is to provide a food composition for removing amyloid plaques, the food composition including ginsenoside F1 or a sitologically acceptable salt thereof.

Another object of the present invention is to provide a feed composition for removing amyloid plaques, the feed composition including ginsenoside F1 or a sitologically acceptable salt thereof.

Still another object of the present invention is to provide a method of removing amyloid plaques, the method including the step of administering ginsenoside F1 to a subject excluding humans.

DETAILED DESCRIPTION OF THE PREFERRED EMBODIMENTS

Figure 1:
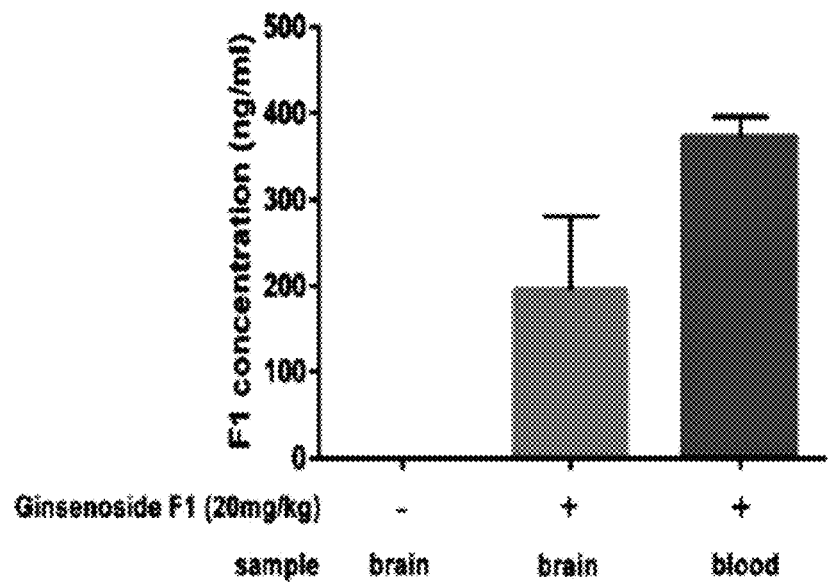
FIG. 1 shows detection of ginsenoside F1 in brain and blood samples of mice fed with a mixture including ginsenoside F1.

In an aspect to achieve the above objects, the present invention provides a food composition for removing amyloid plaques, the food composition including ginsenoside F1 or a sitologically acceptable salt thereof.

As used herein, the term "ginsenoside F1" refers to a compound represented by Chemical Formula 1:

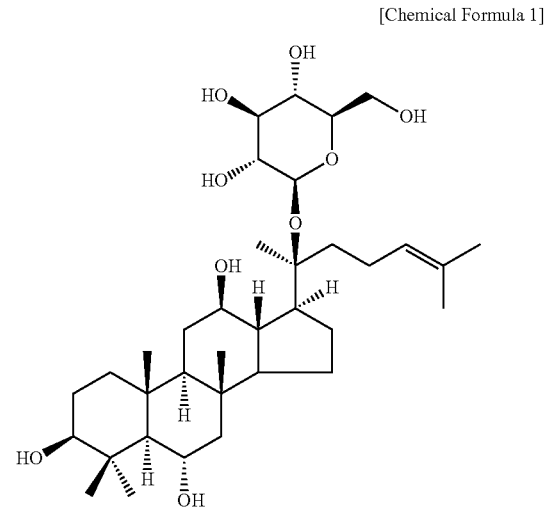

[Chemical Formula 1]

In the present invention, the composition may include ginsenoside F1 in an amount of 0.01% by weight to 99.9% by weight, more preferably 1% by weight to 80% by weight, based on the total weight of the composition, but is not limited thereto. The composition may include ginsenoside F1 in an available amount, determined by those skilled in the art.

When the food is a drink, ginsenoside F1 may be included in an amount of 0.1 g to 1 g, preferably 0.3 g to 0.7 g in 100 ml of the drink. Also, the composition may further include an additive which is commonly used in food compositions to enhance flavor, taste, color, or the like. For example, the composition may include vitamins A, C, D, E, B1, B2, B6 and B12, niacin, biotin, folate, pantothenic acid or the like. The composition may also include a mineral, such as Zinc (Zn), iron (Fe), calcium (Ca), chrome (Cr), magnesium (Mg), manganese (Mn), cupper (Cu) or the like. The composition may also include an amino acid, such as lysine, tryptophane, cysteine, valine or the like. The composition may also be supplemented with food additives, including antiseptics (e.g., potassium sorbate, sodium benzoate, salicylic acid, sodium dehydroacetate, etc.), disinfecting agents (e.g., bleaching powder, higher bleaching powder, sodium hypochlorite, etc.), antioxidants (e.g., butylhydroxyanisole (BHA), butylhydroxytoluene (BHT), etc.), colorants (e.g., tar dye, etc.), color fixing agents (e.g., sodium nitrate, sodium nitrite), bleaching agents (e.g., sodium sulfite), seasoning agents (e.g., MSG, sodium glutamate, etc.), sweeteners (e.g., dulcin, cyclamate, sodium saccharine, etc.), flavoring agents (vanillin, lactones, etc.), blowing agents (alum, potassium D-bitartrate, etc.), fortifying agents, emulsifying agents, thickening agents, coating agents, gum bases, antifoaming agents, solvents, improving agents or the like. The additives may be selected according to food type, and may be used in suitable amounts.

The food composition of the present invention may be prepared by a method generally used in the art, and it may also be prepared by adding raw materials and ingredients which are generally added in the art during the preparation. Further, unlike other common drugs, the food composition may be prepared using foods as raw materials, and thus it has the advantage of avoiding side effects associated with long-term administration of drugs, and it may be very portable.

As used herein, the term "sitologically acceptable salt thereof" refers to a formulation which does not abrogate biological activities and physical properties of ginsenoside F1 included in the food composition.

The sitologically acceptable salt thereof may include those formed from acids which yield non-toxic acid addition salts containing sitologically acceptable anions, for example, inorganic acids such as hydrochloric acid, sulfuric acid, nitric acid, phosphoric acid, hydrobromic acid, hydriodic acid, etc., organic carbonic acid such as tartaric acid, formic acid, citric acid, acetic acid, trichloroacetic acid, trifluoroacetic acid, gluconic acid, benzoic acid, lactic acid, fumaric acid, maleic acid, salicylic acid, etc., or sulfonic acids such as methanesulfonic acid, ethanesulfonic acid, benzenesulfonic acid, p-toluenesulfonic acid, etc. For example, a sitologically acceptable carboxylic acid salt may include a metal salt or an alkali earth metal salt produced by lithium, sodium, potassium, calcium, magnesium, etc., an amino acid salt such as lysine, arginine, guanine, etc., and an organic salt such as dicyclohexylamine, N-methyl-D-glucamine, tris(hydroxymethyl)methylamine, diethanolamine, choline, triethylamine, etc.

As used herein, the term "amyloid plaque" refers to a mass formed by aggregation of amyloid-beta, and an insoluble fibrous protein aggregate that arises from at least 18 inappropriately folded proteins. Presence of amyloid plaques in the brain is known to cause neurodegenerative diseases.

As used herein, the term "amyloid-beta" is a metabolite generated from amyloid precursor protein consisting of 695 amino acid residues by proteases, beta-secretase and gamma-secretase, but not limited to, a peptide consisting of 39 to 43 amino acid residues.

Figure 3:
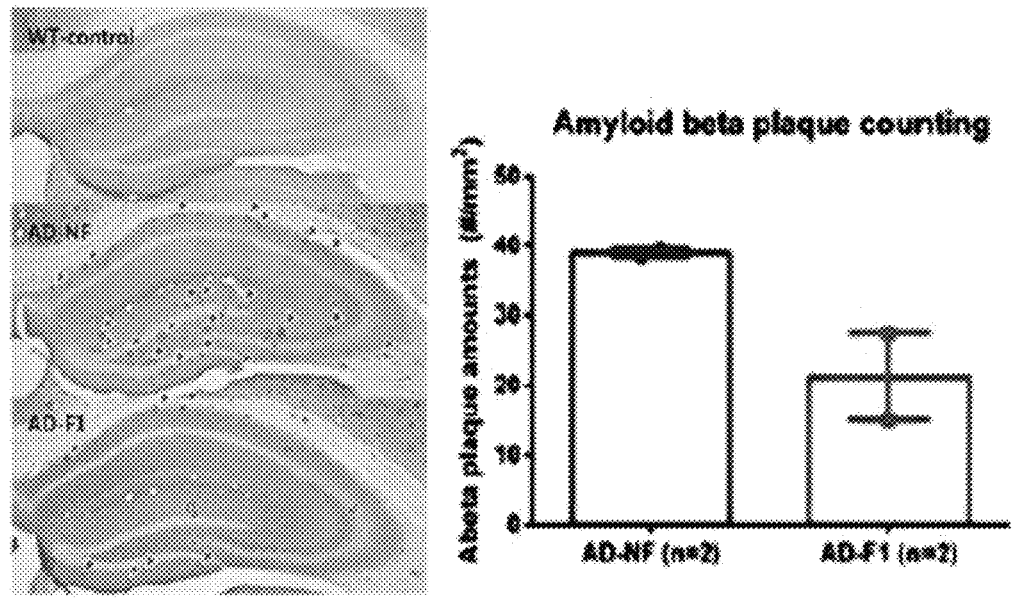
FIG. 3 shows the number of amyloid plaques in the hippocampal area of the brain of Alzheimer mouse models fed with a mixture including ginsenoside F1.

In Experimental Example of the present invention, in order to examine the effect of ginsenoside F1 on the removal of amyloid plaques, the number of amyloid plaques in the hippocampal area of the brain of Alzheimer mouse models fed with a mixture including ginsenoside F1 was counted. As a result, it was found that the number of amyloid plaques in the hippocampal area of Alzheimer mouse models fed with a mixture including ginsenoside F1 was decreased twice, compared to the number of amyloid plaques in the Alzheimer mouse models fed with a normal feed (FIG. 3).

Figure 4:
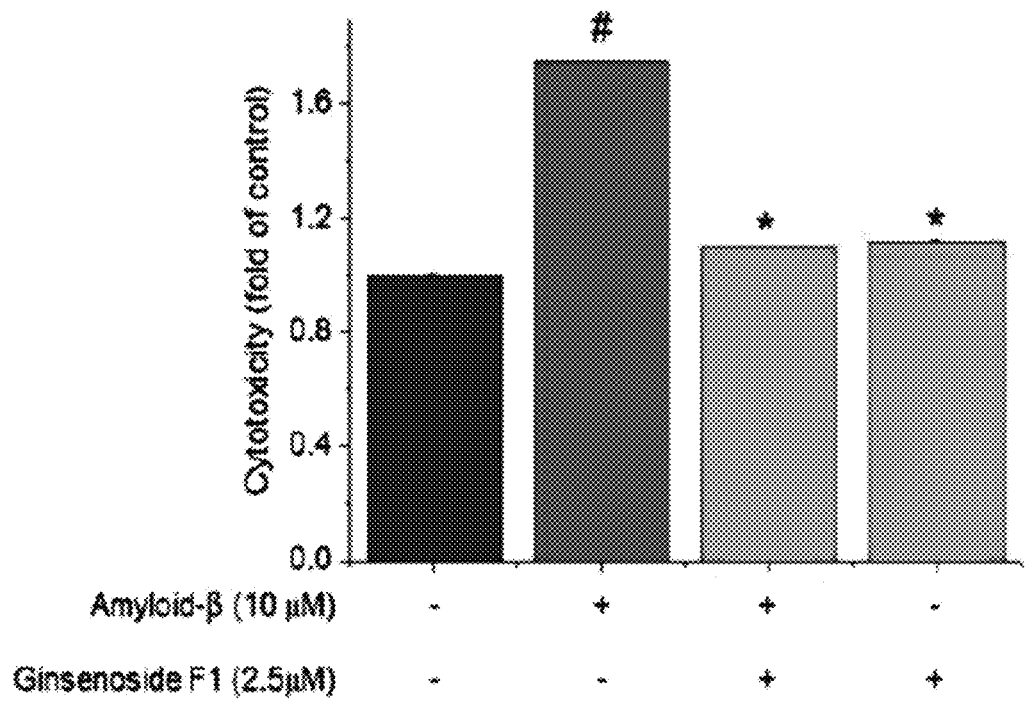
FIG. 4 shows an inhibitory effect of ginsenoside F1 on cytotoxicity induced by amyloid-beta aggregates.

Further, in Experimental Example of the present invention, the inhibitory effect of ginsenoside F1 on cytotoxicity induced by amyloid-beta aggregates was measured by a method of measuring extracellular release of intracellular lactic dehydrogenase caused by cell damage to quantify cell death due to toxicity. As a result, when ginsenoside F1 was treated after treatment of amyloid beta, cytotoxicity was found to be reduced, compared to non-ginsenoside F1-treated group (FIG. 4). This result indicates that cytotoxicity induced by amyloid beta is reduced by ginsenoside F1.

Figure 5:
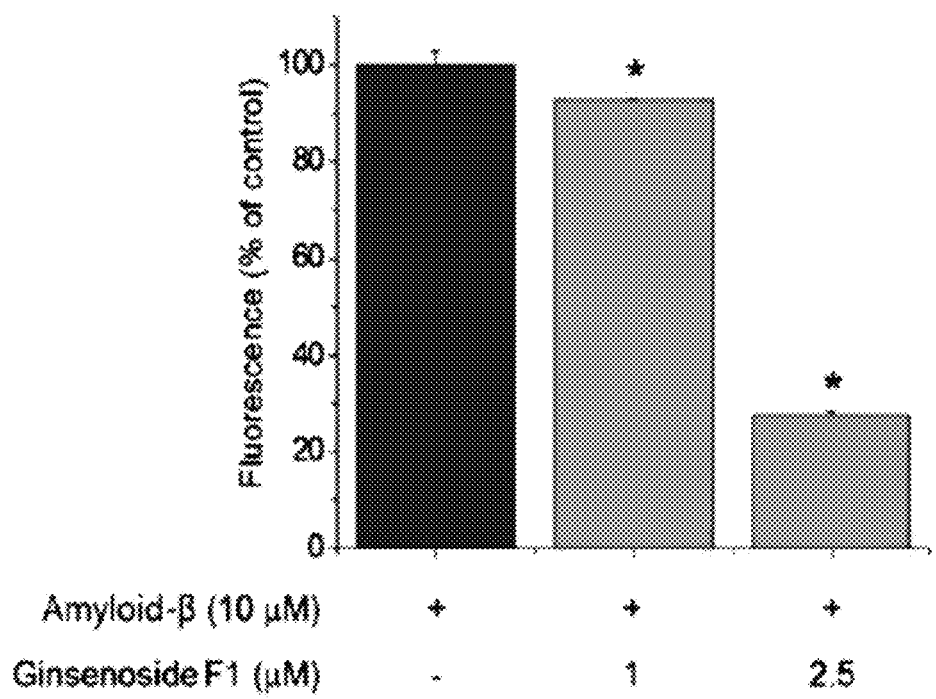
FIG. 5 shows an aggregation-inhibitory effect of 1 to 2.5 uM of ginsenoside F1 on amyloid-beta aggregates.

Further, in Experimental Example of the present invention, changes in fluorescence spectrum by binding of Thioflavin T to amyloid-beta aggregates were measured to examine the aggregation-inhibitory effect of ginsenoside F1 on amyloid-beta aggregates. As a result, when amyloid-beta aggregates were treated with ginsenoside F1, fluorescence intensity was found to be reduced (FIG. 5). This result indicates that ginsenoside F1 reduces aggregation of amyloid-beta to inhibit formation of amyloid plaques.

In the present invention, the composition is characterized by inducing expressions of insulin-degrading enzyme (IDE) and Neprilysin.

In Experimental Example of the present invention, it was examined whether ginsenoside F1 is able to increase expressions of insulin-degrading enzyme and Neprilysin which are proteins capable of degrading amyloid beta aggregates. As a result, it was found that ginsenoside F1 is able to increase mRNA levels of insulin-degrading enzyme and Neprilysin and protein levels thereof (FIGS. 6a to 6d).

In the present invention, the food composition may further include a sitologically acceptable carrier.

As used herein, the term "sitologically acceptable carrier" refers to a carrier or diluent that does not cause significant irritation to an organism and does not abrogate the biological activity and properties of the administered compound. A kind of the carrier applicable in the present invention is not particularly limited, and any carrier may be used, as long as it is a carrier generally used in the art. Non-limiting examples of the carrier may include saline solution, sterile water, Ringer's solution, buffered saline, an albumin injectable solution, a dextrose solution, a maltodextrin solution, glycerol, ethanol or the like. They may be used alone or in a mixture of two or more thereof. The carrier may include a non-naturally occurring carrier.

A kind of the food to which the composition including ginsenoside F1 of the present invention may be added is not particularly limited, and examples thereof may include a variety of drinks, gums, teas, vitamin complexes, health supplement foods, etc. The food composition may further include other components which do not interfere with the effect of removing amyloid plaques, and a kind thereof is not particularly limited. Like common foods, the food composition may include, for example, various herbal extracts, sitologically acceptable food auxiliary additives, or natural carbohydrates as additional components.

The food auxiliary additives may be added during the preparation of health functional foods in various formulations, and may be selected properly by those skilled in the art. Examples thereof may include a variety of nutrients, vitamins, minerals (electrolytes), flavoring agents such as synthetic flavoring agents and natural flavoring agents, colorants and fillers, pectic acid and salts thereof, alginic acid and salts thereof, organic acids, protective colloidal thickening agents, pH modifiers, stabilizers, preservatives, glycerin, alcohols, carbonating agents used in carbonated beverages, etc., but the kind is not limited to these examples.

The food may include a health functional food.

The health functional food is the same term as food for special health use (FoSHU), and refers to a food having high medicinal and medical effects, which is processed to effectively exert a body-regulating function as well as to supply nutrients. The food may be prepared in various forms such as tablet, capsule, powder, granule, liquid, pill, etc., so as to provide a useful effect of ginsenoside F1 on removal of amyloid plaques.

The ginsenoside F1 is a substance which is included in a natural substance, ginseng. Since ginseng has been ingested for a long period of time, its safety has been approved. Therefore, it may be eaten raw or prepared in a food which is intended to be used for removing amyloid plaques.

In another aspect, the present invention provides a feed composition for removing amyloid plaques, the feed composition including ginsenoside F1 or a sitologically acceptable salt thereof.

The feed composition may include a feed additive. The feed additive of the present invention is classified as an auxiliary additive according to Control of Livestock and Fish Feed Act.

As used herein, the term "feed" refers to any natural or artificial diet, meal, etc., or components of such meals intended or suitable for being eaten, taken in, or digested by animals.

A kind of the feed may be, but is not particularly limited to, a feed generally used in the art. Non-limiting examples of the feed may include plant-based feeds, such as grains, nuts, food by-products, seaweeds, fibers, drug by-products, oil, starches, meals, grain by-products or the like; and animal-based feeds such as proteins, inorganic matters, fats, minerals, fats, single cell proteins, zooplanktons, food or the like, but are not limited thereto. They may be used alone or in a mixture of two or more thereof.

In the present invention, the composition may include ginsenoside F1 in an amount of 0.01% by weight to 99.9% by weight, more preferably 1% by weight to 80% by weight, based on the total weight of the composition, but is not limited thereto. The composition may include ginsenoside F1 in an available amount, determined by those skilled in the art.

As used herein, the term "sitologically acceptable salt thereof" is the same as described above.

In the present invention, the feed composition may further include a sitologically acceptable carrier.

As used herein, the term "sitologically acceptable carrier" is the same as described above.

In still another aspect, the present invention provides a method of removing amyloid plaques, the method including the step of administering ginsenoside F1 to a subject excluding humans.

As used herein, the term "subject" refers to all kinds of animals including humans, which may be subjected to removal of amyloid plaques. The animals may be mammals such as cattle, horses, sheep, pigs, goats, camels, antelope, dogs, cats or the like, as well as humans, but are not limited thereto.

As used herein, the term "administration" refers to introduction of the ginsenoside F1 of the present invention into a subject using any suitable method. The ginsenoside F1 of the present invention may be orally or parenterally administered via any of the common routes, as long as it is able to reach the desired tissue.

The administration mode of the ginsenoside F1 according to the present invention is not particularly limited, and the administration may be performed according to the mode generally used in the art. For non-limiting examples of the administration mode, the ginsenoside F1 may be administered orally or parenterally. The ginsenoside F1 according to the present invention may be prepared into various formulations according to the desired administration mode.

With regard to the administration frequency, the ginsenoside F1 of the present invention may be, but is not particularly limited to being, given once a day or several times a day as a divided dosage.

Figure 2A:
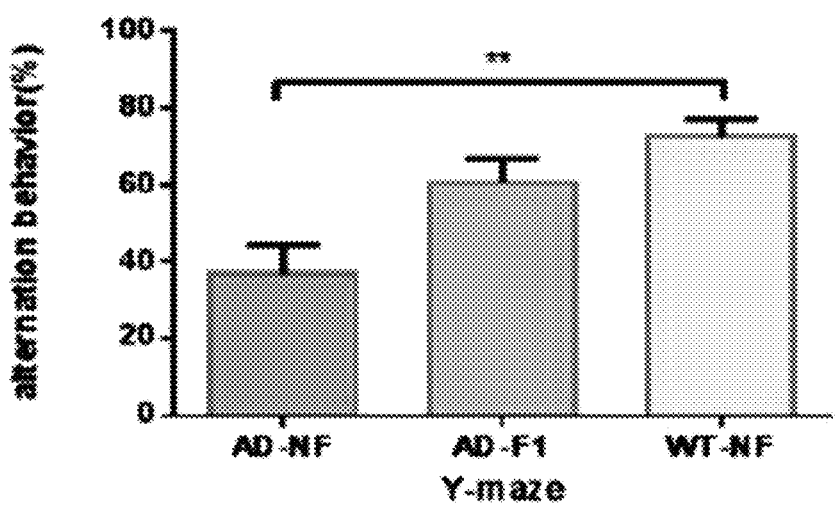
FIG. 2a shows a percentage of alternation behavior of Alzheimer mouse models fed with a mixture including ginsenoside F1.
Figure 2B:
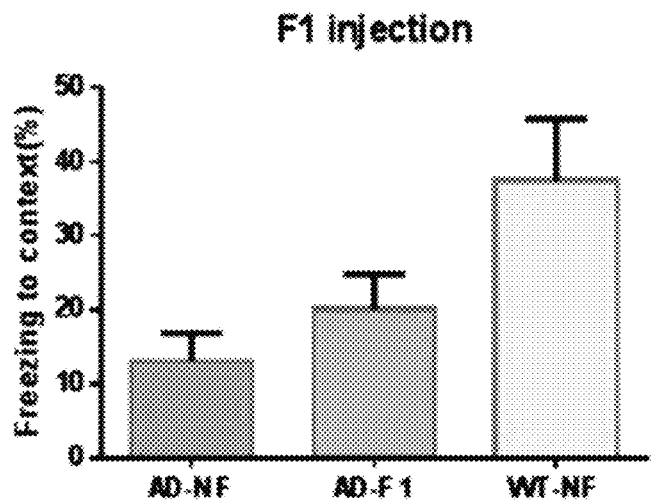
FIG. 2b shows results of contextual fear memory test of Alzheimer mouse models fed with a mixture including ginsenoside F1.

In an embodiment of the present invention, a mixture of ginsenoside F1 was administered to Alzheimer-induced mice, and then Y-maze and contextual fear memory tests were performed to examine whether ginsenoside F1 affects retrieval of memory in mice. As a result, a percentage of alternation behavior was increased to about 1.5 times or more and contextual fear memory was also increased to about 1.5 times in the mice fed with a mixture including ginsenoside F1 (FIGS. 2a and 2b). These results indicate the effect of ginsenoside F1 on retrieval of memory in Alzheimer mouse models.

The method of removing amyloid plaques may reduce amyloid plaques twice or more, compared to a non-ginsenoside F1-treated group.

In Experimental Example of the present invention, when the composition including ginsenoside F1 was administered to Alzheimer mouse models, the number of amyloid plaques in the hippocampus of the mice was decreased twice, compared to the number of amyloid plaques in mice fed with a normal feed (FIG. 3).

Hereinafter, the constitution and effect of the present invention will be described in more detail with reference to Examples and Experimental Examples. However, these Examples and Experimental Examples are for illustrative purposes only, and the scope of the present invention is not intended to be limited by these Examples and Experimental Examples.

Example 1: Preparation of Alzheimer Mouse Models for Animal Test

In order to examine the effect of ginsenoside F1 on retrieval of memory, Alzheimer mouse models were used. Alzheimer mouse models were generated by knock-in of mutated human APP and PS1 transgene into C57/B6XSJL hybrid mice. Mutations introduced in APP and PS1 were reported to increase the production of total amyloid beta.

In detail, tail samples were collected from mice which were born from mating wilt type C57/B6XSJL F1 hybrid female and transgene carrier C57/B6XSJL hybrid male mice. The genotypes of the samples were examined, and mice having the transgene containing Alzheimer disease-related mutations were used. The wild-type mice of the same generation were used as control groups. The mice used in the experiment were mice aged 6 months or older, and only male mice were used for behavioral testing.

Example 2: Preparation of Ginsenoside F1 Mixture to be Administered to Mouse as Experimental Subject In order to administer ginsenoside F1 to mice as experimental subjects, a feed mixture including ginsenoside F1 was prepared.

In detail, feed was mixed with ginsenoside F1 in an amount of 20 mg/kg per day for 3-4 weeks. Since an average daily consumption of feed for a mouse weighing 30 g is 5 g, 35 g of feed powder was mixed with 4.2 mg of ginsenoside F1 to prepare a mixture.

Example 3: Cell Culture for In-Vitro Experiment and Aggregation of Amyloid-Beta

Example 3-1: Cell Culture

One of mouse brain cells, Neuro-2a (N2a) cell was prepared. This cell were cultured in a 90% DMEM medium supplemented with 10% inactivated fetal bovine serum (FBS) under conditions of 5% carbon dioxide, 90% humidity, and 37° C.

Example 3-2: Aggregation of Amyloid-Beta

Amyloid-beta was dissolved in sterile PBS buffer to a concentration of 10 mM, and then left at 37° C. for 48 hours to induce aggregation of amyloid-beta.

Example 3-3: Preparation of Ginsenoside F1

Ginsenoside F1 was dissolved in DMSO to a concentration of 100 mM. Thereafter, the ginsenoside F1 was used after serial dilution.

Experimental Example 1: Verification of Delivery of Ingested Ginsenoside F1 to Brain It was examined whether ginsenoside F1 was effectively delivered to the brains of mice fed with the mixture including ginsenoside F1 prepared in Example 2.

In detail, blood was collected using a capillary tube from the eyes of the mice fed with the feed mixture prepared in Example 2, and thus blood samples were obtained. Further, the mice were anesthetized by intraperitoneal injection of pentobarbital at a concentration of 83 mg/kg. Thereafter, the anesthetized mice were perfused with physiological saline, and the brain tissues were removed to obtain brain samples. The blood and brain samples thus obtained were subjected to LC-MS/MS to analyze the delivery of ginsenoside F1.

The analysis results showed that ginsenoside F1 was detected in the brain and blood samples of the mice fed with the feed mixture including ginsenoside F1, indicating effective delivery of ginsenoside to the brain (FIG. 1).

Experimental Example 2: Animal Test Using Mice Administered with Ginsenoside F1

After the mixture including ginsenoside F1 prepared in Example 2 was administered to the Alzheimer mouse models prepared in Example 1, an animal test was performed in order to examine whether ginsenoside F1 has an effect of memory retrieval.

Experimental Example 2-1: Y-Maze Test

In order to verify the effect of ginsenoside F1 on memory retrieval of Alzheimer mouse models, experimental animals were placed at the center of Y-maze chamber having a width of 60 mm and a height of 125 mm, and allowed to freely explore for 8 minutes to perform Y-maze test.

In detail, Alzheimer mouse models prepared in Example 1 were acclimated to Y-maze chamber for 3 minutes, and later 5 minutes were determined as an actual testing time to analyze behaviors of the experimental animals. Specifically, an entry of a mouse into one of the three arms was calculated as one entry, and the total number of entries was examined. Successive three entries into the three different arms were calculated as one alternation behavior. A percentage of alternation behavior was analyzed by the following equation:

Percentage of alternation behavior=(the number of alternation behavior)/(total number of arm entries−2)*100(%).

The analysis results showed that the percentage of alternation behavior of Alzheimer mouse models fed with the mixture including ginsenoside F1 was increased about 1.5 times or more, compared to that of Alzheimer mouse models fed with a normal feed including no ginsenoside F1 (FIG. 2a).

Accordingly, it was confirmed that ginsenoside F1 exhibits an effect of memory retrieval in Alzheimer mouse models.

Experimental Example 2-2: Contextual Fear Memory Test

In order to verify the effect of ginsenoside F1 on memory retrieval of Alzheimer mouse models, Alzheimer mouse models were subjected to a contextual fear memory test.

In detail, Alzheimer mouse models prepared in Example 1 were placed in a fear conditioning chamber. At 180 seconds after the experimental animal entered the chamber, an electric shock of 0.5 mA was applied for 2 seconds. At 30 seconds after application of the electric shock, the experimental animal was taken out of the chamber and returned to its home cage (fear memory conditioning).

At 24 hours after the fear memory conditioning, the same experimental animal was placed in the same fear conditioning chamber. After the experimental animal was placed in the chamber, its behavior was observed for 5 minutes. If the experimental animal showed no visible movement except for breathing, it was regarded as 'freezing'. The total time spent freezing was recorded. Freezing for 5 minutes was considered as a standard, and 'contextual fear memory' of experimental animals was analyzed.

The test results showed that the contextual fear memory of Alzheimer mouse models fed with the mixture including ginsenoside F1 was increased about 1.5 times or more, compared to that of Alzheimer mouse models fed with a normal feed including no ginsenoside F1 (FIG. 2b).

Accordingly, it was confirmed that ginsenoside F1 exhibits an effect of memory retrieval in Alzheimer mouse models.

Experimental Example 3: Examination of Number of Amyloid Plaques in Mouse Administered with Ginsenoside F1

The number of amyloid plaques in the hippocampal area of the brain of Alzheimer mouse models of Example 1 which were fed with the feed mixture prepared in Example 2 was counted.

In detail, the mice were anesthetized by intraperitoneal injection of pentobarbital (83 mg/kg). Thereafter, the anesthetized mice were perfused with physiological saline and a formaldehyde solution, and the brain samples were removed and stored in the formaldehyde solution. 24 hours later, the brain samples were stored in a 30% sucrose solution. About 48 hours later, when the brain samples sank to the bottom of the sucrose solution, the brain samples were frozen, followed by cryosectioning into 40 μm-thick sections. The brain sections were put in a PBS solution containing 0.02% sodium azide, and refrigerated (Preparation of brain section samples).

After preparation of the brain section samples, amyloid plaques were stained by the following method (washing was performed with physiological saline for 10 minutes between individual steps, and the washing was repeated four times):

a) The prepared brain section samples were left in a 0.3% hydrogen peroxide solution at room temperature for 30 minutes.

b) The prepared brain section samples were left in a blocking solution (0.1% BSA, 0.2% Triton X-100, 2% goat-serum in PBS) at room temperature for 1 hour.

c) Thereafter, the brain section samples were treated with rabbit anti-amyloid beta antibody at a ratio of 1:1000, and then incubated at 4° C. for 48 hours.

d) The brain section samples of step c) were treated with HRP conjugated goat anti-rabbit antibody at a ratio of 1:2000, and incubated at room temperature for 2 hours.

e) The brain section samples of step d) were incubated in an ABC solution at room temperature for 1 hour.

f) The brain section samples of step e) were incubated in a DAB solution at room temperature for 8 minutes, and then added with 30 μl of a 0.3% hydrogen peroxide solution, followed by incubation at room temperature for 1 minute and 30 seconds.

g) The brain section samples stained through step a) to step f) were put on a slide, and mounted with xylene-added cytoseal to count the number of amyloid plaques in the hippocampal area of the brain.

The measurement results showed that the number of amyloid plaques in the hippocampal area of Alzheimer mouse models fed with the mixture including ginsenoside F1 was decreased twice, compared to that of Alzheimer mouse models fed with a normal feed (FIG. 3).

These results indicate that ginsenoside F1 exhibits an excellent effect on the removal of amyloid plaques, and a therapeutic effect on diseases caused by accumulation of amyloid plaques, such as dementia, etc.

Experimental Example 4: Inhibitory Effect of Ginsenoside F1 on Cytotoxicity Induced by Aggregated Amyloid-Beta The cells cultured in Example 3-1 were treated with aggregated amyloid-beta and ginsenoside F1, and then cytotoxicity was measured using an LDH assay kit. Sample preparation steps for experiments were performed as follows:

a) The brain tissue cells cultured in Example 3-1 were left in a 48-well cell culture medium free of fetal bovine serum.

b) Amyloid-beta aggregated in Example 3-2 was added to the medium of step a) to a concentration of 10 uM, followed by incubation for 30 minutes.

c) Ginsenoside F1 prepared in Example 3-3 was added to the medium of step b) to a concentration of 100 uM, followed by incubation for 48 hours.

d) Culture supernatants of step b) and step c) were transferred to 48-well plates, and refrigerated.

After the sample preparation steps, a catalyst and a staining solution provided by a manufacturer of the LDH kit (Roche) were mixed at a ratio of 1:45 to prepare a reaction mixture. Thereafter, each of the culture supernatants prepared in step d) was transferred to a 96-well plate at a concentration of 100 μl/well, and 100 μl of the reaction mixture was added to each well. Then, absorbance at 490 nm was measured using a microplate reader (LDH assay).

The measurement results showed that cytotoxicity of a group treated with only amyloid-beta was increased 1.4 times, compared to a non-treated group. In contrast, cytotoxicity of a group treated with ginsenoside F1 after treatment of amyloid-beta was decreased so that there was no difference with the non-treated group. Further, a group treated with only ginsenoside F1 showed little cytotoxicity, compared to non-treated group (FIG. 4).

These results showed that ginsenoside F1 inhibits amyloid-beta-induced cytotoxicity, and also, ginsenoside F1 itself does not exhibit cytotoxicity in brain cells. Consequently, it was confirmed that ginsenoside F1 is a safe substance in the brain cells, and has an inhibitory effect on amyloid-beta-induced cytotoxicity at the same time.

Experimental Example 5: Measurement of Aggregation Inhibition of Aggregated Amyloid-Beta by Ginsenoside F1

In order to examine an inhibitory effect of ginsenoside F1 on aggregated amyloid-beta, changes in fluorescence spectrum by binding of Thioflavin T to amyloid-beta aggregates were measured.

In detail, amyloid-beta aggregated in Example 3-2 was added to the cell culture medium free of fetal bovine serum to a concentration of 10 uM, followed by incubation for 30 minutes. Thereafter, ginsenoside F1 prepared in Example 3-3 was added to the medium by varying the concentration at 1 uM and 2.5 uM, followed by incubation for 48 hours.

Meanwhile, a method of measuring aggregation of amyloid-beta is as follows:

a) Thioflavin T was dissolved in 100 mM glycine buffer (pH 8.5) to a concentration of 300 uM.

b) Before use, 300 uM Thioflavin T solution was diluted 50-fold.

c) 100 μl of the diluted Thioflavin T solution was added to 100 μl of the sample after completion of culture, and the sample was left in the dark at room temperature for 30 minutes.

d) Fluorescence intensity at an excitation wavelength of 450 nm and an emission wavelength of 490 nm was measured using a multi-mode microplate reader.

The measurement results showed that the fluorescence intensity was very high in a group treated with only amyloid-beta. In contrast, when ginsenoside F1 was treated, the fluorescence intensity was decreased, and in particular, when 2.5 uM of ginsenoside F1 was treated, the fluorescence intensity was decreased under half of the intensity (FIG. 5). Accordingly, it was confirmed that ginsenoside F1 decreases aggregation of amyloid-beta.

Experimental Example 6: Induction of Expression of Amyloid-Beta Aggregate-Degrading Proteins by Ginsenoside F1

In order to examine whether ginsenoside F1 is able to induce expressions of insulin-degrading enzyme (IDE) and Neprilysin (NPE) which are proteins capable of degrading amyloid beta aggregates, changes in mRNA levels and protein levels were measured by real-time PCR and Western blot.

In detail, ginsenoside F1 prepared in Example 3-3 was added to a cell culture medium free of fetal bovine serum by varying the concentration at 1 uM and 2.5 uM, followed by incubation for 24 hours. A method of measuring mRNAs expression levels of insulin-degrading enzyme and Neprilysin which are proteins capable of degrading amyloid beta aggregates is as follows:

a) A culture medium was removed from a 60 mm-cell culture plate where culture was completed.

b) 600 ul of a reagent provided by a manufacturer of an RNA extraction reagent (TaKaRa) were added to the medium of step a) and dissolved.

c) The dissolved solution of step b) was transferred to a 1.5 ml-centrifuge tube, and 300 ul of chloroform solution was added thereto, followed by centrifugation to collect a supernatant containing RNA.

d) The supernatant collected in step c) was mixed with an equal amount of isopropanol, followed by centrifugation to obtain RNA pellet.

e) The RNA pellet obtained in step d) was washed with 75% ethanol, and dried to obtain RNA pellet with high purity.

f) The RNA pellet obtained in step e) was dissolved in diethylpyrocarbonate (DEPC)-treated distilled water to quantify RNA using a nano-drop machine.

g) The RNA obtained in step f) was reacted at 50° C. for 2 hours using a reagent provided by a manufacturer of a reverse transcriptase kit (Solgent) to synthesize cDNA.

h) cRNA synthesized in step g) was mixed with primers of insulin-degrading enzyme, Neprilysin, and beta-actin (β-actin) prepared by a primer manufacturer, GenoTech Corp, and a reagent provided by a manufacturer of a SYBR premix Ex Taq kit (TaKaRa), and then mRNA transcription levels of insulin-degrading enzyme and Neprilysin were measured by a real-time PCR machine (real-time PCR).

Figure 6A:
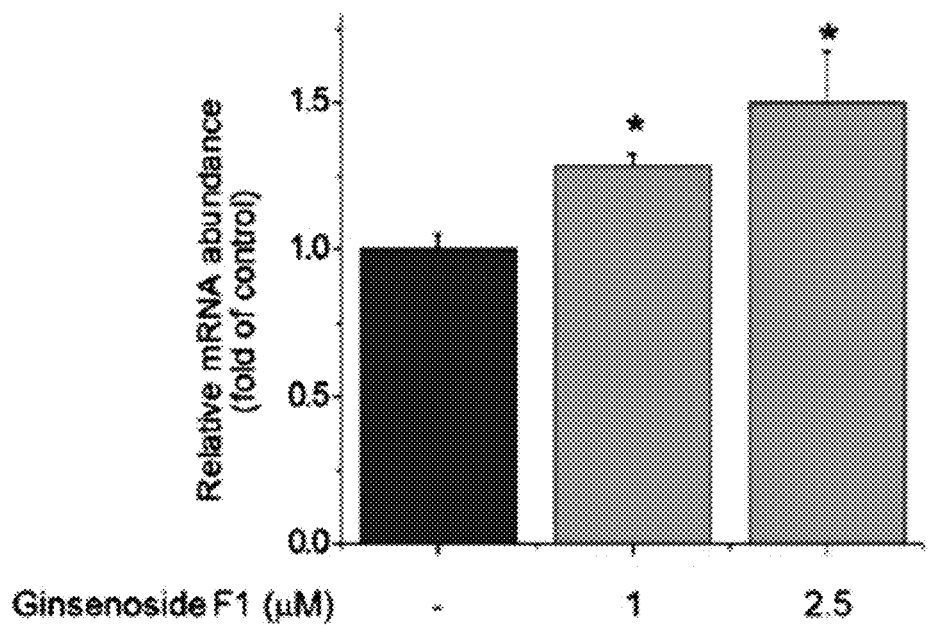
FIG. 6a shows an mRNA expression level of insulin-degrading enzyme upon treatment of ginsenoside F1.
Figure 6B:
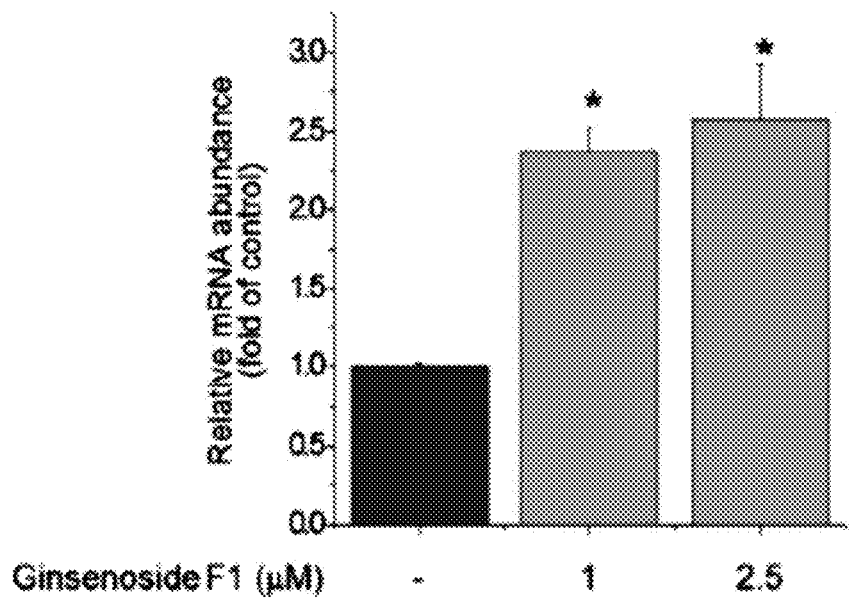
FIG. 6b shows an mRNA expression level of Neprilysin upon treatment of ginsenoside F1.

The measurement results showed that treatment of ginsenoside F1 increased mRNA transcription levels of insulin-degrading enzyme and Neprilysin. Specifically, when 2.5 uM of ginsenoside F1 was treated, the mRNA transcription level of insulin-degrading enzyme was increased 1.5 times or more, and the mRNA transcription level of Neprilysin was increased 2.5 times or more (FIGS. 6a and 6b).

Meanwhile, a method of measuring protein expression levels of insulin-degrading enzyme and Neprilysin which are proteins capable of degrading amyloid beta aggregates is as follows:

a) A culture medium was removed from a cell culture plate where culture was completed.

b) 1 ml of 1×PBS (pH 7.4) was added to the medium of step a), and cells were collected using a cell scraper to be transferred to a 1.5 ml-centrifuge tube, followed by centrifugation to obtain a cell pellet.

c) 100 ul of a protease inhibitor-added cell lysis buffer was added to the pellet obtained in step b) and mixed to lyse cells, followed by centrifugation to obtain a supernatant.

d) Proteins of the supernatant obtained in step c) were quantified using a reagent provided by a manufacturer of a protein quantification kit (iNtRON).

e) A staining solution for reducing SDS-PAGE and the proteins quantified in step d) were mixed and boiled for 5 minutes, and then dropped on a 12% SDS-PAGE gel, followed by electrophoresis at 70 volts for 1 hour and 30 minutes.

f) The SDS-PAGE gel electrophoresed in step e) was transferred to a PVDF membrane using a membrane transfer apparatus.

g) The PVDF membrane transferred in step f) was blocked with 5% skim milk for 1 hour.

h) The PVDF membrane of step g) was washed with a 1×TBST solution, and reacted with mouse-derived insulin-degrading enzyme, Neprilysin, and beta-actin (β-actin) primary antibodies for 2 hours.

i) The membrane of step h) was washed with the 1×TBST solution, and then reacted with HRP-conjugated anti-rabbit immunoglobulin secondary antibody or HRP-conjugated anti-mouse immunoglobulin secondary antibody for 2 hours.

j) A substrate solution and an amplification solution provided by a manufacturer of a Western blot detection kit (iNtRON) were mixed at a ratio of 1:1 to prepare a reaction mixture. The membrane of step i) was washed with the 1×TBST solution, and then 2 ml of the reaction mixture was reacted with the membrane. Thereafter, fluorescence and chemical imaging analyzers were used to detect proteins (Western blot).

Figure 6C:
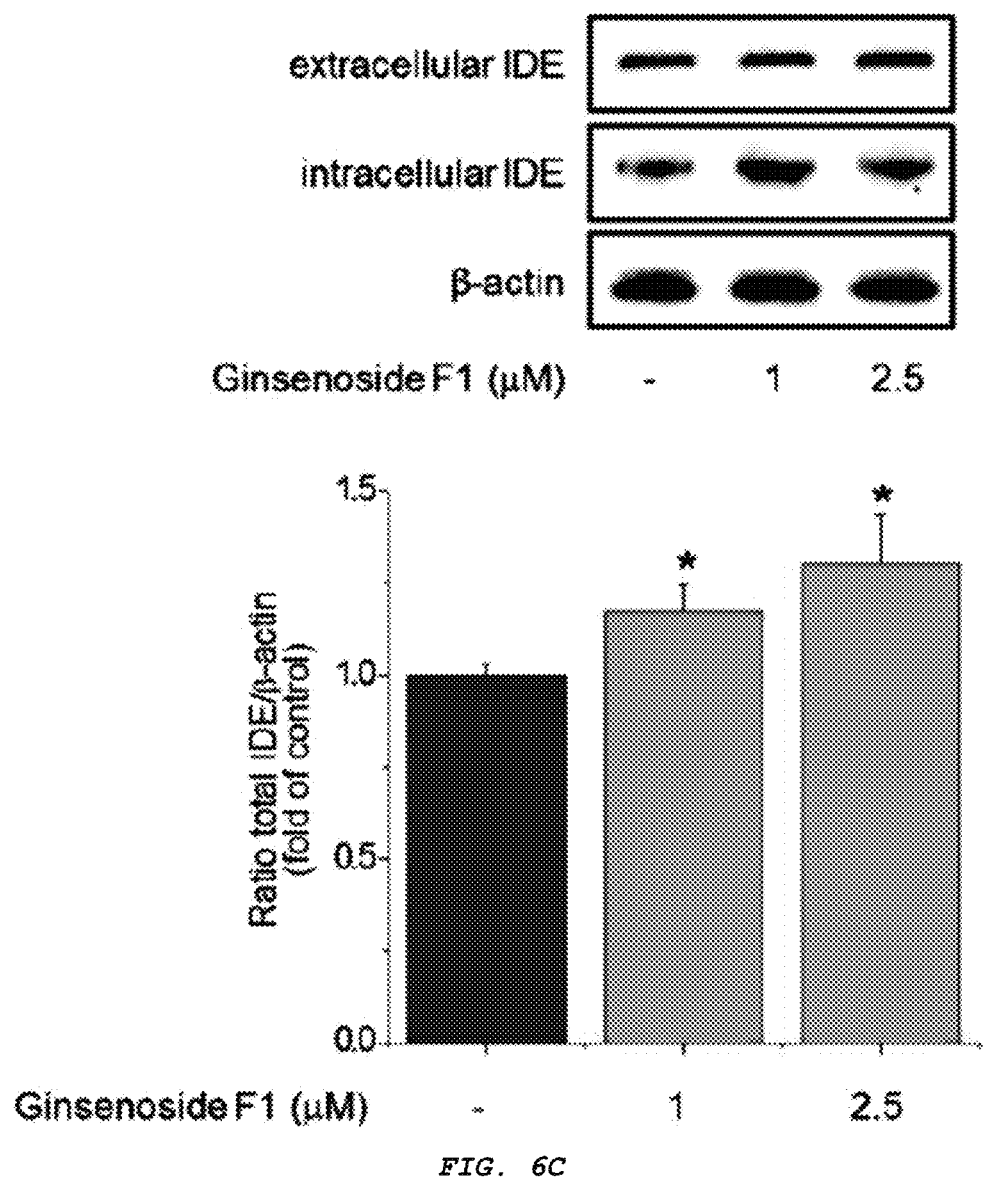
FIG. 6c shows a protein expression level of insulin-degrading enzyme upon treatment of ginsenoside F1.
Figure 6D:
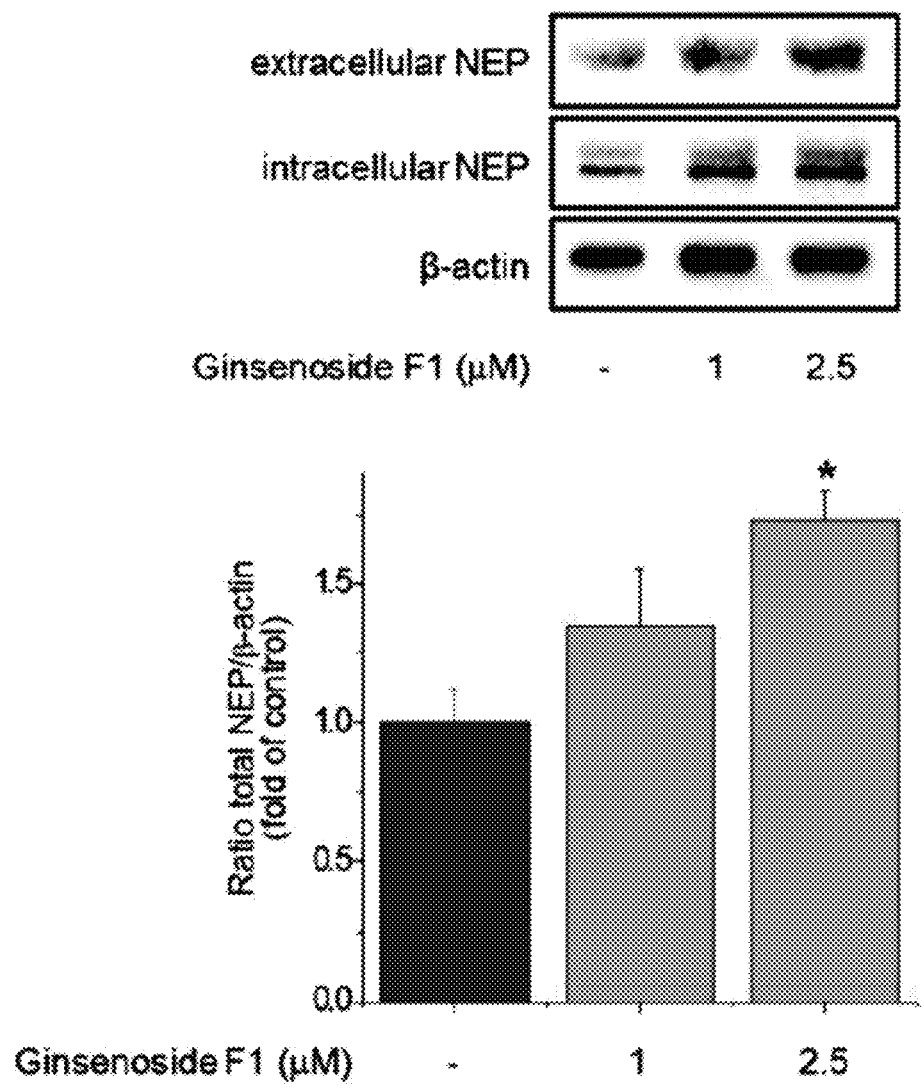
FIG. 6d shows a protein expression level of Neprilysin upon treatment of ginsenoside F1.

The measurement results showed that a protein expression level of insulin-degrading enzyme was increased 1.3 times or more in a group treated with 2.5 uM of ginsenoside F1, compared to a control group (FIG. 6c). Further, a protein expression level of Neprilysin was increased 1.5 time or more in a concentration-dependent manner (FIG. 6d).

Accordingly, it was confirmed that ginsenoside F1 is able to remove amyloid plaque aggregates by increasing expression levels of insulin-degrading enzyme and Neprilysin.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

According to the present invention, a mixture including ginsenoside F1 is used to remove amyloid plaques in the hippocampal area of the brain, thereby improving retrieval of memory.

What is claimed is:

1. A method of removing amyloid plaques formed by aggregation of amyloid-beta, comprising the step of administering composition comprising ginsenoside F1 or an acceptable salt thereof to a subject.

2. The method of claim 1, wherein the method is used to decrease amyloid plaques twice or more, compared to a subject administered with no ginsenoside F1.

3. The method of claim 1, wherein the composition comprises ginsenoside F1 in an amount of 0.01% by weight to 99.9% by weight, based on the total weight of the composition.

4. The method of claim 1, wherein the composition further comprises a sitologically acceptable carrier.

5. The method of claim 1, wherein the composition induces expressions of insulin-degrading enzyme (IDE) and Neprilysin (NPE).

6. A method of removing amyloid plaques formed by aggregation of amyloid-beta, comprising the step of administering ginsenoside F1 to a brain cell.

* * * * *